United States Patent [19]

Arima et al.

[11] Patent Number: 5,293,326

[45] Date of Patent: Mar. 8, 1994

[54] ULTRASONIC INSPECTION AND IMAGING INSTRUMENT

[75] Inventors: Yukio Arima, Tsukuba; Hiroaki Yanagimoto, Ibaraki; Yuichi Kunitomo, Tsuchiura; Shouya Makihara; Tetsuyoshi Tominaga, both of Ibaraki, all of Japan

[73] Assignee: Hitachi Construction Machinery Co., Ltd., Tokyo, Japan

[21] Appl. No.: 719,510

[22] Filed: Jun. 24, 1991

[30] Foreign Application Priority Data

Jun. 29, 1990 [JP] Japan .................. 2-172370

[51] Int. Cl.⁵ ............... G01N 29/00; G09G 5/00
[52] U.S. Cl. .................. 364/579; 364/506; 73/619; 345/127
[58] Field of Search ........... 364/579, 506, 507, 188, 364/189, 413.25; 73/619, 620, 621, 626; 340/712, 731; 395/157, 159, 161

[56] References Cited

U.S. PATENT DOCUMENTS

| | | | |
|---|---|---|---|
| 4,141,347 | 2/1979 | Green et al. | 128/660.05 |
| 4,649,380 | 3/1987 | Penna | 340/731 |
| 4,872,130 | 10/1989 | Pagano | 364/507 |
| 5,027,110 | 6/1991 | Chang et al. | 340/731 |
| 5,042,305 | 8/1991 | Takishita | 73/625 |
| 5,146,556 | 9/1992 | Hullot et al. | 395/159 |

FOREIGN PATENT DOCUMENTS

2623997  6/1989  France .
62-226375  10/1987  Japan .

Primary Examiner—Thomas G. Black
Assistant Examiner—Michael Zanelli
Attorney, Agent, or Firm—Fay, Sharpe, Beall, Fagan, Minnich & McKee

[57] ABSTRACT

An ultrasonic inspection and imaging instrument is characterized by storing reduced image examples (images by means of reduced image display data obtained by scaling down picture display data) of an ultrasonic measurement picture beforehand, together with measurement conditions at the time the measurement picture is obtained prior to a scale-down imaging process. When the measurement is started or the measurement conditions are otherwise changed, the measurement conditions are set as those obtained from the measurement picture prior to the scale-down processing with one of the reduced image examples thus selected as an index while a list of image examples is indicated on a display and read from a memory unit for ultrasonic measuring purposes. When a reduced image example or what is similar to the example desired by an operator is selected, proper measurement conditions are automatically set in the ultrasonic inspection and imaging instrument. When the operator wants to change or switch the measurement picture, moreover, he/she is able to make ultrasonic measurement on confirming what the subsequent image is like or what an image is desired to be selected by means of the reduced image example beforehand.

14 Claims, 5 Drawing Sheets

ULTRASONIC INSPECTION AND IMAGING INSTRUMENT

BACKGROUND OF THE INVENTION

1. Technical Field

The present invention relates to ultrasonic inspection and imaging instruments and more particularly to an ultrasonic inspection and imaging instrument in which when parts of the same kind are inspected, proper measurement conditions can readily be set to ensure that inspection efficiency is improved.

2. Related Art

An ultrasonic inspection and imaging instrument is used for observing vertical and transverse sectional images of an object under examination by controlling a scanning unit capable of moving a focusing-type probe in X-, Y- and Z-directions while these images obtained from a predetermined location of the object are displayed on a screen. In an instrument of this sort, proper measurement conditions have to be set before ultrasonic measurement is carried out to obtain a desired image. The measurement conditions include setting values (e.g., of scanning strokes and pitches) in the scanning unit, setting values (e.g., of gains and gate positions) in a transducer circuit of an ultrasonic detection unit, and setting display forms (e.g., display in the form of binary values, density display and color display) on an imaging unit.

The respective measurement conditions to be set or altered as described above should therefore correspond to conditions of inspection in order to obtain the image desired to be observed. To facilitate the alteration of such measurement conditions, there are the following known methods: a method of indicating a list of file names relating to measurement conditions on a display so that a selector (operator) may select proper measurement conditions from the list by reference to the file names; another of indicating a list of detailed set values of measurement conditions on a screen so that an operator may read the list and select proper measurement conditions therefrom or amend some of them to set optimum ones; and the like. In the latter case where the list is relied upon, however, the operation is very troublesome as it is necessary to alter the set value in each circuit or unit under the control of a microprocessor unit (MPU). In the former case where the file names are referred to, on the other hand, a decision being made on the measurement conditions depends on only the file names.

In practice, the operator may keep a notebook or the like in which the contents have been written in detail, designate a file name and repeat the regeneration of one measurement image after another corresponding thereto until finding an image with measurement conditions to be selected. Generally, the alteration of measurement conditions is made not to drastically change the set values but to modify part of any set value step by step. The alteration above is normally made by matching minor numerical values in the detailed list of set values with the conditions under which a desired picture is obtained. This operation is not only troublesome but also susceptible to operator-induced mistakes in selecting improper conditions because of misjudgment. Apart from this, it is frequently required to switch one measurement picture over to another when an object under examination is inspected; in such a case, a measurement depth, a measurement range (thickness) and a measurement area are particularly modified. When a measurement sample is changed, moreover, the set value in each component unit needs altering and measurement conditions with different set values will otherwise have to be found.

The foregoing problems make it burdensome for beginners to operate an ultrasonic inspection and imaging instrument. Even those skilled in the operation of such an instrument may often fail to find proper measurement conditions until an image is actually displayed. It is therefore extremely difficult for those inexperienced in ultrasonic thickness measurement to alter measurement conditions, which makes them unable to decide whether the image obtained from the alteration of the measurement conditions or the switching of the measurement picture is fit for the purpose.

SUMMARY OF THE INVENTION

An ultrasonic inspection and imaging instrument embodying the present invention wherein a scale-down imaging process is applied to display data on an ultrasonic measurement picture to create reduced image display data, and wherein a memory for storing a plurality of data corresponding to the reduced image display data together with measurement conditions when measurement pictures corresponding to the reduced image display data are collected, is characterized in that a plurality of reduced measurement pictures (hereinafter called 'reduced image examples') are displayed so that they are not overlapped in such a way that the display thereof is based on the plurality of reduced image display data stored in the memory and that when one of the reduced image examples thus displayed is selected, a given object under examination is subjected to ultrasonic measurement with the measurement conditions stored therein, which also correspond to the then reduced image display data, whereby its measurement picture is indicated on the display.

As it has been arranged that a list of several image examples is used to obtain measurement conditions with the reduced image examples as indexes when measurement conditions are changed, an operator is allowed to automatically set the measurement conditions by only selecting the same image as a desired one or as resembling a desired one. When the operator wants to change the measurement picture or switch it to another one, he/she is able to select corresponding measurement conditions on confirming what an image to be selected is like or what image is desired to be selected by means of the image examples.

An object of the present invention is therefore to provide an ultrasonic inspection and imaging instrument which permits any person who is inexperienced in ultrasonic measurement to set proper measurement conditions for an object under examination.

Another object of the present invention is to provide an ultrasonic inspection and imaging instrument which permits setting and alteration of measurement conditions by only selecting the image example indicated on a display.

Still another object of the present invention is to provide an ultrasonic inspection and imaging instrument which makes it possible to readily have an accurate grasp of an overall image showing how the measurements taken result in an actual image.

A further object of the present invention is to provide an ultrasonic inspection and imaging instrument capable of improving inspection efficiency at the time various objects are inspected.

BRIEF DESCRIPTION OF THE DRAWINGS

FIGS. 3(a-3(c)) are diagrams illustrating the relation between the process of setting measurement conditions by means of image examples and a display picture in the embodiment shown.

DESCRIPTION OF THE PREFERRED EMBODIMENT

Figure 1:
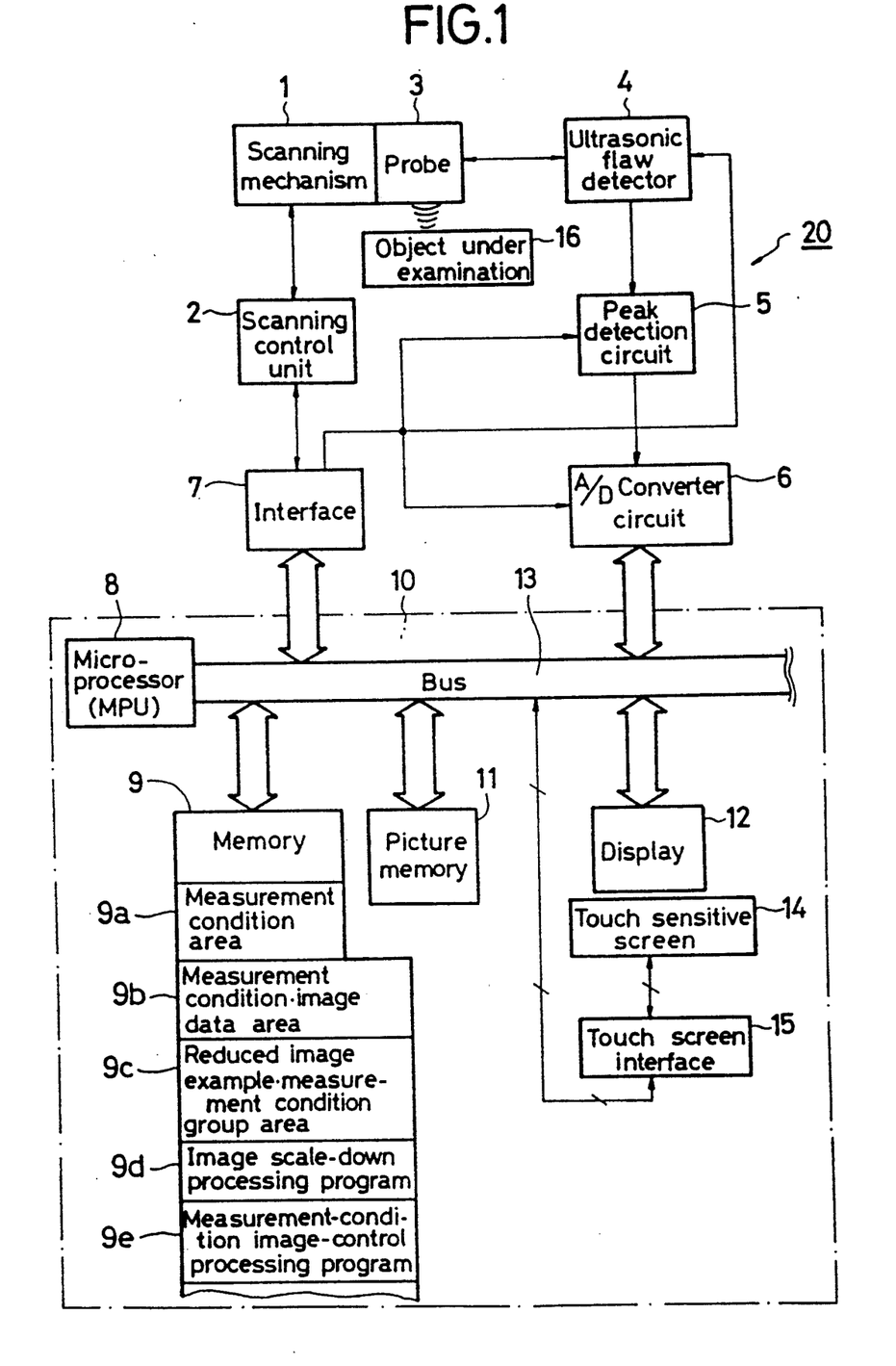
FIG. 1 is a block diagram of an ultrasonic inspection and imaging instrument embodying the present invention.

FIG. 1 shows an ultrasonic inspection and imaging instrument 20 and a scanning mechanism 1 having an XYZ moving mechanism. A focussed probe 3 is fitted to the scanning mechanism 1 and used for the main scanning of an object 16 under examination in the X-direction and for the subscanning of that object in the Y-direction. The ultrasonic inspection and imaging instrument 20 obtains measured values from which an A-scope image at each measurement point is obtained by the XY scanning, based on which it produces and displays display data on a B-scope image and display data on a C-scope image. Incidentally, an interface such as a junction face to be inspected exists in a position at a certain depth from the surface of the object 16 under examination in this embodiment.

The scanning mechanism 1 is controlled by a scanning control unit 2, which is in turn controlled by a picture processor unit 10 via an interface 7. The probe 3 is connected to an ultrasonic flaw detector 4 consisting of a pulser.receiver and the like. The ultrasonic flaw detector 4 applies a pulse signal from its transmission terminal to the probe 3 with a predetermined measurement period in response to a control signal from the picture processor unit 10 to drive the probe 3. The probe 3 converts into an electrical signal the echo obtained from the object 16 under examination with respect to the ultrasonic wave generated then and the electrical signal thus converted is received as an echo reception signal by the reception terminal of the ultrasonic flaw detector 4 from the probe 3. The electrical signal is then amplified before being detected and the signal thus obtained is applied to a peak detection circuit 5.

The peak detection circuit 5 provides a gate in position using the echo reception signal thus detected to detect a peak value of the echo portion required and supplies the peak value to an A/D converter circuit 6. The gate positioning depends on the set signal received from the picture processor unit 10 via the interface 7. The peak detection circuit 5 sets the gate by detecting, for instance, a surface echo and performing time counting in accordance with the set signal.

The A/D converter circuit 6 converts the analog signal of the peak value obtained in accordance with the control signal from the picture processor unit 10 into a digital value at 256 8-bit stages, for instance. The digital value is sent to a bus 13 as input data made processable by a microprocessor unit (MPU) 8.

As a result, the peak value is detected by the peak detection circuit 5 at each measurement point where the object under examination 16 is scanned by the probe 3 in the X-direction and the value thus detected is delivered to the MPU 8. The MPU 8 stores data on these peak values at the measurement points corresponding thereto in a memory 9 sequentially.

In addition to the microprocessor unit 8, a control panel (not shown), the memory 9 for storing various programs and data, a picture memory 11, a display 12 and the like are connected to the bus 13. A touch-sensitive screen 14 is fitted to the display 12 and connected via a touch-sensitive screen interface 15 to the bus 13. The touch-sensitive position is read in the MPU 8 through an interruption process.

Moreover, the memory 9 is provided with a measurement condition area $9a$, a measurement condition image data area $9b$, and a reduced image example measurement condition group area $9c$. The memory 9 also stores with an image scale-down processing program $9d$, a measurement-condition image-control processing program $9e$, a display processing program and the like.

With 640×400 dots constituting pixels on the screen of the display 12, the picture memory 11 has a storage area in which display data corresponding to each pixel is stored and the display 12 forms a so-called bit map display. In such a bit map, an area where the display data on a picture for ultrasonic measurement is actually stored is normally smaller than that of the display picture and set to, e.g., 480×320 dots.

Figure 3A:
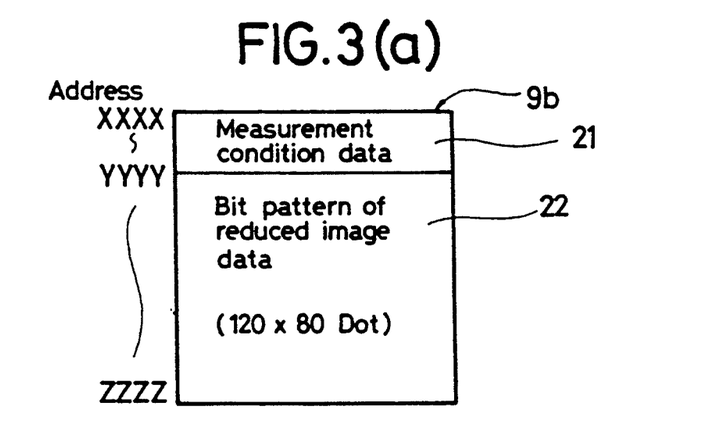

In the measurement condition area $9a$, there are stored parameters for use in determining various measurement conditions and set values in units and circuits to be controlled for measuring purposes (hereinafter called 'parameters, etc.'). The measurement condition image data area $9b$ consists of, as shown in FIG. 3(a), a measurement condition area 21 for storing parameters, etc. and an image area 22 for storing scale-down display data (in this case, image data which is in the state of bit pattern data). Moreover, the data stored in the image area 22 is equivalent in amount to the display pattern data (120×80 dots) obtained by scaling down the display data (480×320 dots) on the measurement picture stored in the image memory 11 to 1/16.

Parameters, etc. in the case of scanning are respective coordinate values of X, Y, Z at the center of an image while scanning measurement is carried out and in the case of X, Y planar scanning, respective strokes and measurement pitches during the X, Y planar scanning being carried out. In the case of ultrasonic flaw detection, moreover, parameters, etc. are an applied voltage an amplification gain, a gate width, etc. with respect to an ultrasonic transducer, whereas in the case of display information, they are an image display color and a luminance conversion parameter. In addition to those stated above, the parameters, etc. further include various set values in circuits, units and the like as other controlled objects.

Figure 3B:
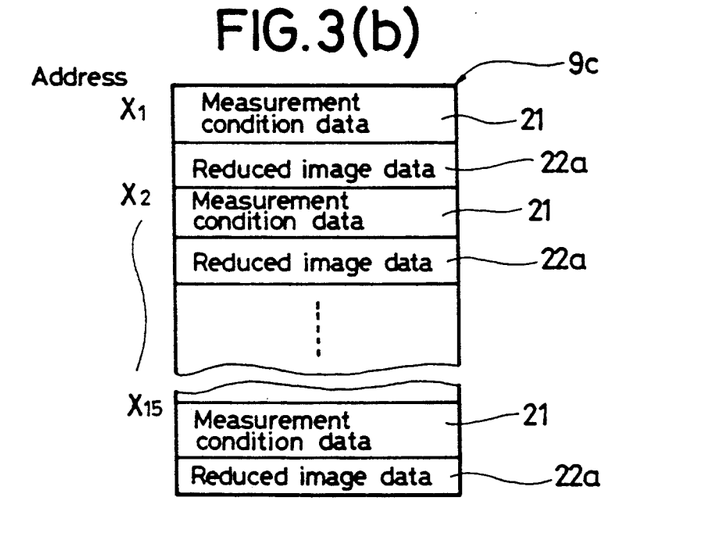
Figure 3C:
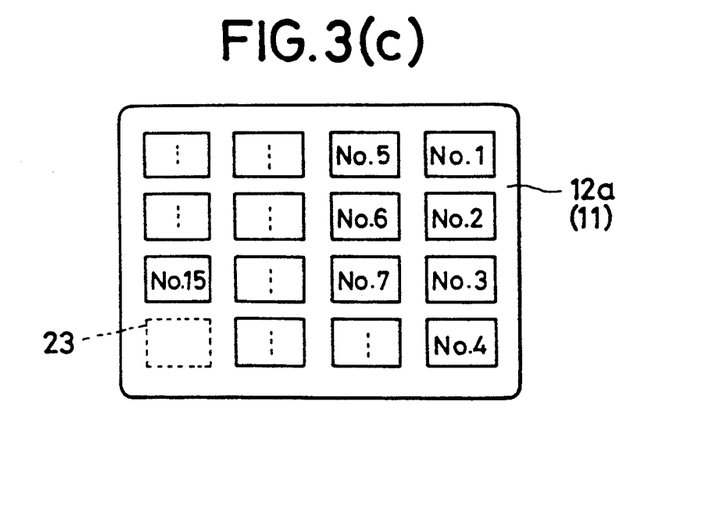

The reduced image example.measurement condition group area $9c$ has a storage area 15 times as great as that in the measurement condition image data area $9b$. The storage area is, as shown in FIG. 3(b), divided into 15 areas with respective head addresses $X_1$-$X_{15}$ for control. The data in the measurement condition.image data area are transferred to the 15 divided areas, so that 15 images of those data are to be stored in the divided areas, respectively. Of the data stored in the 15 divided areas identified as $X_1-X_{15}$, the reduced image data in image areas 22a are allotted, according to subscript No. 1–No. 15 of the head addresses Xi, to the respective reduced image display areas framed on the screen 12a of the display 12 shown in FIG. 3(c). Consequently, the storage area on the image memory 11 is controlled so that the reduced image data in the respective image areas 22 are stored correspondingly. As shown in FIG. 3(c), the reduced image data in each image area 22a is displayed with a thin line frame. When the display data in each image area 22a is transferred to the image memory 11, a frame bit pattern corresponding to the display is added to the data.

The image scale-down processing program 9d is activated by the MPU 8 when a work selection menu is indicated on the display 12 and when 'measurement condition memory' is selected via the touch-sensitive screen 14. Simultaneously with the activation of this program, the MPU transfers the parameters, etc. in the measurement condition area 9a stored with the present measurement conditions to measurement condition area 21 in the measurement condition.image data area 9b. The reduced display data (120×80 dots) resulting from scaling down the measurement picture display data (in this case, 480 ×320 dots) in the picture memory 11 to 1/16 is created. Further, the reduced display data are transferred to the image area 22 in the measurement condition image data area (see FIG. 3(a)) and stored therein as reduced image data. The storage data in the picture memory 11 is then cleared and the reduced display data are transferred to a reduced image display area 23 (see FIG. 3(c)) of the picture memory 11. Since the screen 12a corresponds in relationship to the picture memory 11 as shown in FIG. 3(c), the reduced image display area 23 on the screen 12a also indicates the storage area corresponding to the picture memory 11.

Figure 4:
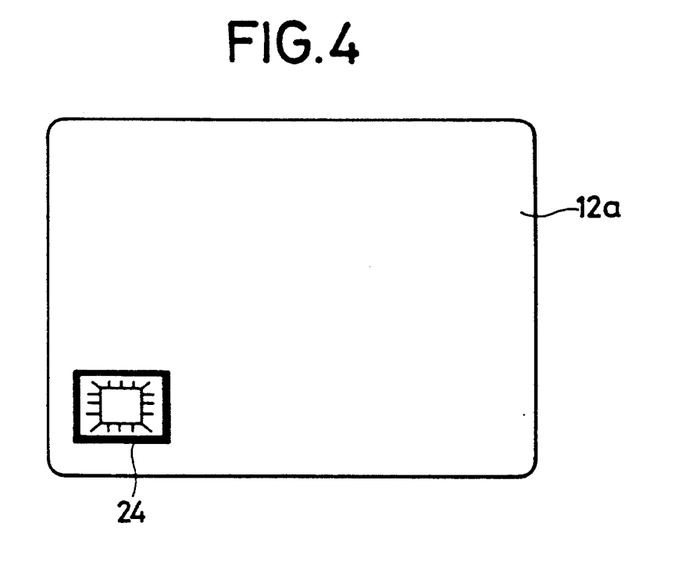
FIGS. 4 to 8 inclusive, are diagrams illustrating pictures on displays, the pictures being displayed in conformity with reduced image creation and storage process in the embodiment shown.

The reduced image display area 23 is allotted to the storage area in a lower left-hand corner position on the screen 12a relative to the picture memory 11 as shown in FIG. 3(c). When the reduced display data (bit pattern data as reduced image data) is transferred to the storage area corresponding to the reduced image display area 23 relative to the picture memory 11, a thick pattern data frame is added to enclose the area in the on-state as shown in FIG. 4. The reduced image thus displayed is, as shown in FIG. 4, clearly distinguishable from the other areas on the screen of the display 12.

The data in the picture memory 11 is transferred by the display processing program to be subsequently activated to the display 12 and displayed as a picture 24 with a thick frame as shown in FIG. 4. When the display is completed, the image scale-down processing program 9d activates the measurement-condition image-control processing program 9e.

The measurement-condition image-control processing program 9e is additionally activated by the MPU 8 while 'measurement condition regeneration' in the work selection menu stays in the on-condition. When this program is activated after the image scale-down processing program, the MPU 8 transfers the reduced image data obtained from the past image scale-down processing and stored in the reduced image example.-measurement condition group area 9c from the image areas 22a to the respective storage areas No. 1–No. 15 in the picture memory 11 allotted correspondingly, together with the bit data having thin frames. Further, the MPU 8 activates the display processing program, displays pictures of FIG. 5 in the respective reduced image display areas No. 1–No. 15 on the screen of the display 12 and waits for a coordinate input signal (indicating pixel coordinates) from the touch-sensitive screen 14.

Figure 5:
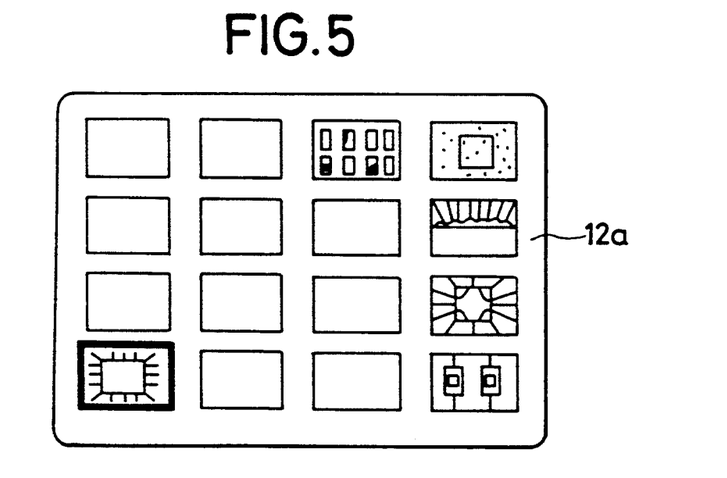

On receiving the coordinate input signal from the touch-sensitive screen 14 via a touch screen interface 15, the MPU 8 controls the list of image examples on the display 12 shown in FIG. 5 by attaching No. 1–No. 15 shown in FIG. 3(c) accordingly and decides which one of the frame numbers has been designated. The reduced image examples controlled by these numbers correspond to the respective address positions of subscripts of the head addresses $X_1-X_{15}$ in the reduced image example.measurement condition group area 9c shown in FIG. 3(c).

The MPU 8 subsequently executes the program and transfers the parameters, etc. and the reduced image data (bit pattern data of the measurement picture) in the measurement condition.image data area 9b to the reduced image example.measurement condition group area 9c (area of head address Xi, i=1–15) corresponding to the number (i) designated via the touch-sensitive screen 14. Further, the MPU 8 transfers the reduced image data in the measurement condition.image data area 9b to an area (see FIG. 3(c)) in the picture memory 11 corresponding to the number (i) designated via the touch-sensitive screen 14. At this time, the data in the reduced image display area 23 of the image memory 11 is cleared and then the display processing program is activated to have the display data in the picture memory 11 transferred to the display 12 and displayed thereon.

Figure 6:
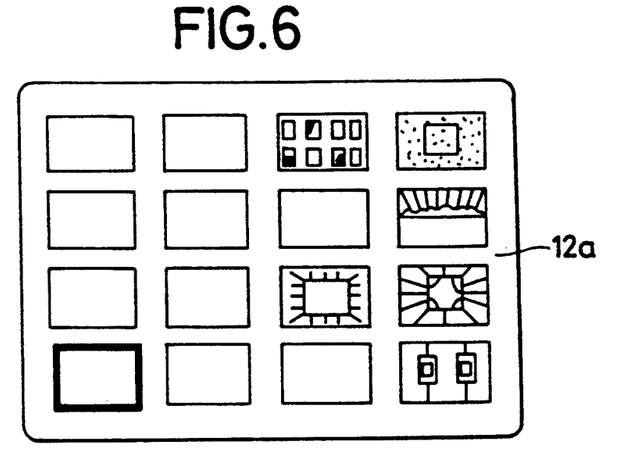

The reduced image data is thus created and indicated before being catalogued in the memory 9. FIG. 6 shows an example in which the No. 7 reduced image display area has been selected and the reduced image data in the reduced image display area 23 has been transferred to the image data 22a with the head address $X_7$ in the reduced image example.measurement condition group area 9c corresponding to the No. 7 reduced image display area. After being catalogued, the data stored in the reduced image example.measurement condition group area 9c is further stored in an external storage medium such as a floppy disk, a hard disk or the like, so that it is utilized separately in this instrument or other similar instruments.

When the 'measurement condition regeneration' in the work selection menu is selected, the measurement-condition image-control program 9e is executed, whereby the MPU 8 reads reduced image data from the image area 22a in the reduced image example.measurement condition group area 9c corresponding to the number designated via the touch-sensitive screen 14 and transfers the data thus read to the reduced image display area 23 in the picture memory 11. In addition to the processing above, the MPU 8 reads measurement conditions (e.g., parameters, etc.) corresponding to the reduced image data read from the divided area with the head address Xi including the image area 22a and transfers them to the measurement condition area 9a. Incidentally, when the data stored in an external storage medium such as a floppy disk, a hard disk or the like is employed, it is necessary to transfer a pair of necessary measurement conditions and reduced image data as data from the external storage medium to the reduced image example.measurement condition group area 9c beforehand.

Figure 2:
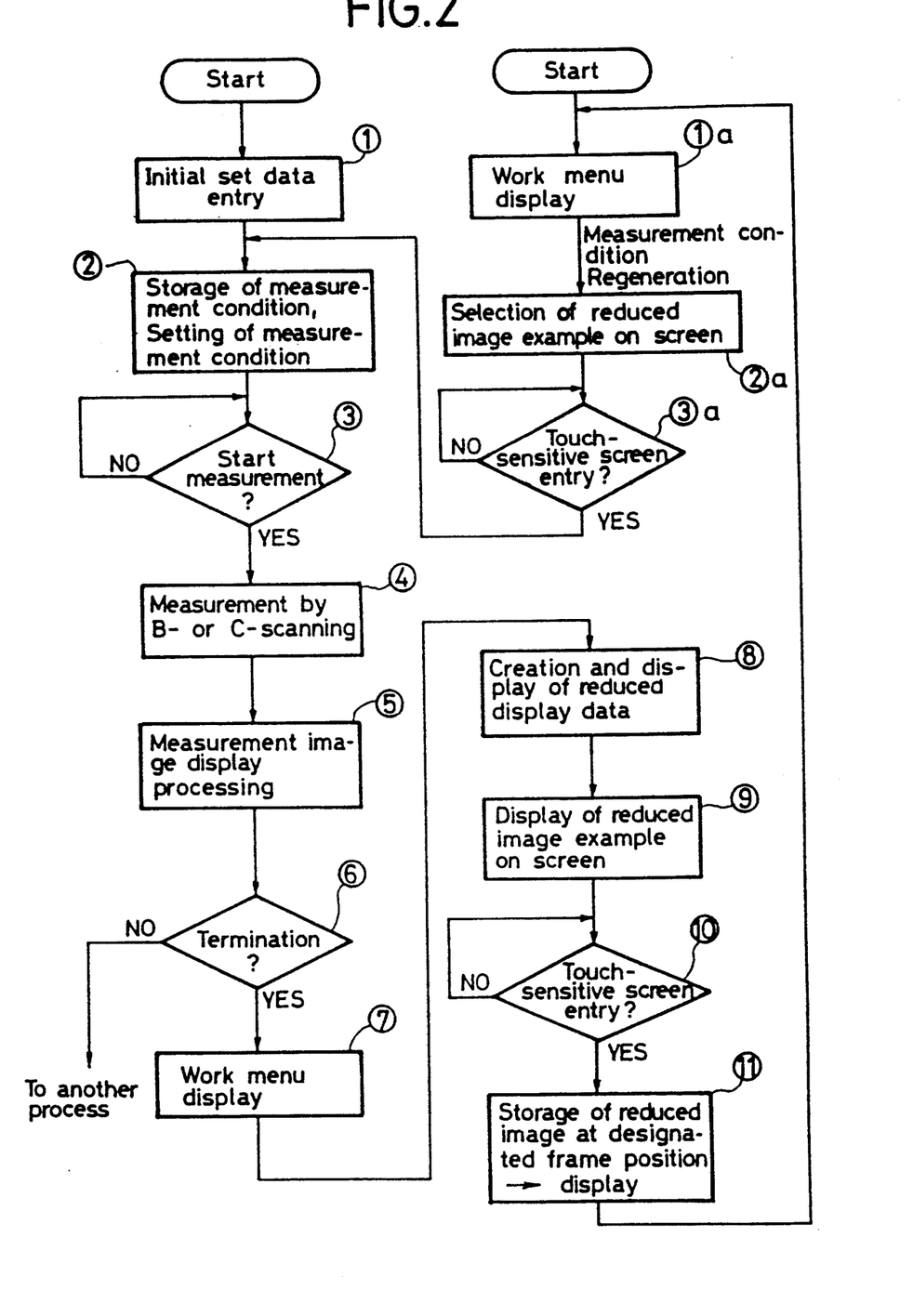
FIG. 2 is a flowchart illustrating an overall measuring process centering on a reduced image creating process with measurement conditions in the instrument embodied above.

A description will subsequently be given of an overall measuring process centering on a reduced image creating process with measurement conditions in the picture processor unit 10 with reference to FIG. 2.

At Step 1, various measurement conditions including initial data on the focal length of the probe 3, the thickness of the object 16 under examination and the like are fed from the control panel. At Step 2, the measurement conditions set at this time are stored in the measurement condition area 9a and the parameters, etc. (measurement conditions) stored in the measurement condition area 9a are set via the scanning unit 2, the ultrasonic flaw detector 4, the peak detection circuit 5, the A/D converter circuit 6 and the like.

The measurement conditions at this time include setting a mode in which either B- or C-scanning, a scanning start position and the like with respect to the scanning unit 2, the generation period of a transmission pulse with respect to the ultrasonic flaw detector 4, the gate width, the gate setting timing and the like in the peak detection 1: circuit 5, and the sampling period an the like in the A/D converter circuit 6 are determined as described above. The gate width for detecting the peak is set to a period ranging from, e.g., 0.1 μs to several μs, whereas the gate position is set in agreement with the focal position of the probe 3 and in terms of, e.g., elapsed time after the detection of a surface echo.

At Step 3, the process enters a loop waiting for a measurement start key to be pressed and when the measurement start key on the control panel is pressed, the units and the circuits involved are operated with the measurement conditions designated and stored in the measurement condition area 9a at Step 4, so that the probe 3 starts B- or C-scanning the object 16 under examination. In response to the scanning, multi-gradation data on the peak value obtained corresponding to each measurement point is stored as display data at an address in the picture memory 11 corresponding to XY coordinates (or XZ coordinates) in conformity with the XY coordinates (or XZ coordinates) of the present scanning position each time the scanning is carried out.

Figure 7:
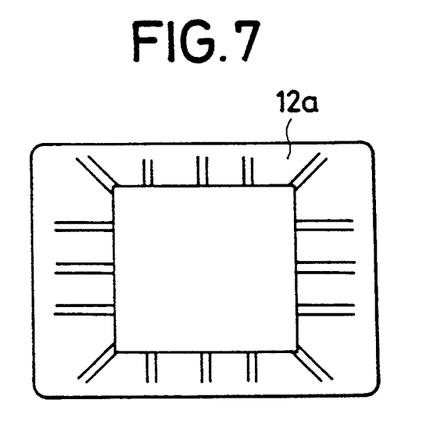

At Step 5, the display data stored in the picture memory 11 is transferred to the video memory of the display 12 and a picture is displayed under the control of the built-in controller of the display 12. FIG. 7 illustrates a C-scope image of the object 16 under examination, by way of example.

When measurement is thus made with the predetermined measurement conditions, the measurement picture as an ultrasonic image is stored as display data in the picture memory 11 and indicated on the display 12.

At Step 6, a decision is made on whether the measurement is terminated and if YES, the work selection menu for inviting the following process is displayed. The operator then starts selecting the next operation. If an item, 'measurement condition storage', is selected from those indicated in the work selection menu, Step 8 is followed and the image scale-down processing program 9d is activated.

Consequently, the display data in the present picture memory 11 is reduced by the image scale-down processing program 9d to a 1/16 bit pattern and stored in the image area 22 as a reduced image display data. The measurement conditions in the measurement condition area 9a are also transferred to the measurement condition area 21 in the measurement condition.image data area 9b and further to the reduced image display area 23 in the image memory 11 to obtain the display picture shown in FIG. 4. At this time, any portion other than the reduced image display data on the picture memory 11 is cleared.

At Step 9, the measurement-condition image-control program 9e is executed and the reduced image examples, together with measurement conditions, stored in the reduced image example.measurement condition group area 9c are transferred via the bus 13 onto the picture memory 11 in sequence. The list of display images shown in FIG. 5 is thus obtained.

Any blank area without an image within a thin frame indicates an unused storage area. The touch-sensitive screen 14 is controlled with the sequential numbers shown in FIG. 3(c) relative to the image examples on the display 12 as listed by means of the measurement-condition image-control program 9e as shown in FIG. 5.

At Step 10, an input via the touch-sensitive screen 14 is waited for and if the No. 1 range is touched, it is tantamount to the selection of a right-hand upper image position in the image example of FIG. 5. As the image display condition in FIG. 4 is actually instantly transferred to what is shown in FIG. 5, the image plane of FIG. 5 looks as if it were switched on in the instant that the item 'measurement condition storage' is selected for operation on the part of the operator.

When the operator selects and touches the blank area corresponding to No. 7 as described above, the reduced image display data and its measurement conditions temporarily stored in the measurement condition.image data area 9b framed in the lower left-hand corner on the screen are transferred to the area with the head address $X_7$. Further, the reduced image data corresponding to No. 7 in the reduced image display area of the picture memory 11 is transferred, so that a picture is displayed on the screen 12a of the display 12 as shown in FIG. 6.

As set forth above, the operator can store and keep each data on measurement conditions and the corresponding reduced image display data (image example) as its index by only touching a given blank area once with reference to the list of image examples indicated. When the operator touches not a blank area but No. 2, for instance, on which an image example has already been indicated, it is needless to say possible to update the reduced image display data, together with its measurement condition data, in the image area 22a (area with the head address $X_2$) corresponding to No. 2 in the reduced image example.measurement condition group area 9c.

A description will subsequently be given of setting measurement conditions in accordance with the image examples in the picture processor unit 10 with reference to FIG. 2. The measurement conditions in the measurement condition area 9a are also transferred to the measurement condition area 21 in the measurement condition.image data area 9b at this time.

When the operator initially displays the work selection menu and selects the item 'measurement condition regeneration' at Step 1a, the reduced image data (reduced image example) in each image area 22a in the reduced image example.measurement condition group area 9c is read and transferred via the bus 13 onto the picture memory 11 at Step 2a. The list of display images of FIG. 6 is thus obtained.

Figure 8:
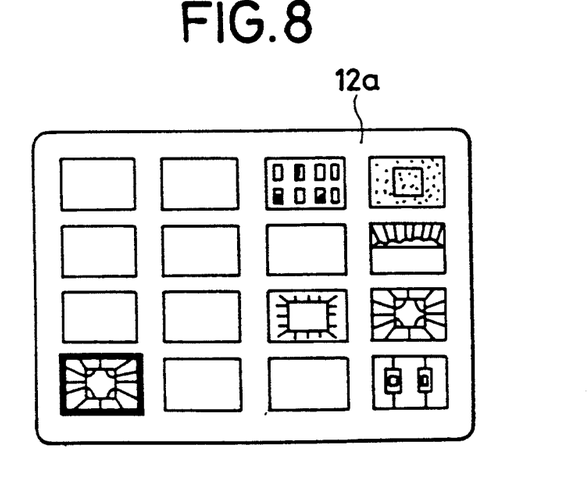

At Step 3a, the process enters a loop waiting for the touch sensitive screen 14 to be touched and when a No. 3 image, for instance, out of the reduced images indicated on the screen of the display 12 is touched by the operator, the measurement-condition image-control program 9e is executed and the reduced image data in the image area 22a (corresponding to the No. 3 reduced image display area) with the head address $X_3$ in the reduced image example.measurement condition group area 9c corresponding to the reduced image display area No. 3 is transferred to the reduced image display area 23 of the picture memory 11. A reduced image is copied and transferred to the frame in the left-hand lower corner on the screen as shown in FIG. 8. Then the measurement conditions stored in the measurement condition area 21 with the head address $X_3$ in the reduced image example.measurement condition group area 9c are transferred to the measurement condition area 9a.

Subsequently, Step 2 is followed and measurement conditions by the parameters, etc. of the measurement conditions thus transferred to the measurement condition area 9a are set in the various units and circuits. The set values in the respective component units in the instrument are read from the measurement condition area 9a, whereby the scanning control unit 2, the ultrasonic flaw detector 4 and the image display parameters, etc. are set in conformity with the set values. At Step 3, an input via the measurement start key is waited for and when the measurement start key is pressed, measurement is made in accordance with the measurement conditions corresponding to the reduced image thus selected.

On condition that the inspection instrument performs the processes described above, the operations of changing and switching set values can be concentrated on only the designation of image examples. Provided an experienced operator has measurement conditions with a given number of image examples stored after subjecting the object 16 under examination to ultrasonic measurement, the operator will be able to make various kinds of measurement even though he/she is inexperienced in subjecting the object 16 under examination and those of the same kind to ultrasonic image inspection. As a result, setting errors because of differences between individuals are prevented and this makes possible inspections with high data reproducibility. If there is the image example obtained from the object under examination involved, it may be used as an index to determined measurement conditions. Therefore, the operator can readily select and set measurement conditions by directly selecting the reduced image example without the operation of setting or changing data in each component unit or circuit, or selecting another set value to change or switch the image intended. Moreover, the operator will be able to instantly understand what an image resulting from measurement is like without estimating its profile. In case the operator is inexperienced, he/she is prevented from overlooking or misreading the modified set value as he/she is requested only to designate an image example. As the data available is highly reliable, it facilitates the supposition of an actual image resulting from measurement and the acquisition of the whole image. Moreover, as the operation of changing or switching measurement conditions to be set can be dispensed with, operation efficiency is improvable significantly.

As set forth above, there are listed maximum 15 kinds of measurement conditions with reduced image examples as indexes. However, the number of measurement conditions is not limited to 15. When a display having an approximately 10- to 14-inch display screen is employed, the number of reduced image examples may range from about 5 to 15. Moreover, the reduction ratio need not necessarily be 1/16.

In addition, it is possible to inspect various kinds of objects under examination by storing multiple kinds of reduced image examples accompanied with such measurement conditions as to correspond to the kinds thereof in external storage units, including floppy and hard disks, and transferring the reduced image display data and parameters, etc. of the reduced image example of the object under examination corresponding to an object to be examined to the reduced image example.measurement condition group area 9c. More reduced image examples may be stored in those cases described above, if the reduced image example.measurement condition group area 9c is provided with more space.

In the embodiment shown, there has been shown an example in which the peak value is first detected to obtain a measurement picture or a reduced image. However, the measured value is not limited to the peak value but any one obtainable from a picture by detecting an echo in terms of its echo level, path and the like.

In the embodiment shown, further, the data is transferred to the reduced image display area 23 of the picture memory 11 to display the reduced image once when the reduced image is catalogued and when the measurement conditions relative to the reduced image selected are read out. However, these processes are not always required. When the reduced image is stored, it may be transferred directly to any blank area in the reduced image example.measurement condition group area 9c for storage. When the measurement conditions corresponding to the reduced image selected at the time of measurement are sent to the measurement condition area 9a, those corresponding to the reduced image just selected may be transferred thereto.

In the embodiment shown, the reduced image data and the measurement conditions are stored and utilized by one and the same ultrasonic inspection and imaging instrument. However, not only the ultrasonic inspection and imaging instrument used to obtain the measurement picture but also another one for use in making similar measurement can be utilized for setting and selecting measurement conditions as long as there exist the measurement conditions stored in the reduced image example.measurement condition group area 9c and the data combined with the reduced picture of the measurement picture obtained under the measurement conditions. Any other instrument stated above need not obtain such a measurement picture to create data for combining its reduced picture with the measurement conditions. Therefore, the ultrasonic inspection and imaging instrument according to the present invention need not always have the function of creating reduce image data on a measurement picture and data on the measurement conditions combined with the measurement picture.

We claim:

1. An ultrasonic inspection and imaging instrument for detecting an echo obtainable from an object under examination by two-dimensionally scanning the object under examination using an ultrasonic probe to obtain display data and for displaying a measurement picture of the object under examination corresponding to said two-dimensional scanning, said instrument comprising:

a memory unit for storing data of a plurality of images and a plurality of measurement conditions corresponding to said plurality of images, including measurement conditions under which said measurement picture is obtained;

a processor unit for concurrently displaying a plurality of images without being overlapped on a display screen according to the plurality of image data stored in said memory unit, for obtaining from said memory unit the measurement conditions stored corresponding to image data of an image selected from said plurality of stored images, and for displaying the measurement picture of the object under examination on the display screen by subjecting the object under examination to said two-dimensional scanning in accordance with the selected image; and means for two-dimensionally scanning the object under examination responsive to a signal from the processor unit that automatically presets the scanner with the measurement conditions in accordance with a user-indicated one of the displayed images.

2. An ultrasonic inspection and imaging instrument as claimed in claim 1, wherein said processor unit includes means for creating reduced image display data by performing a data scale-down imaging process at a predetermined ratio from the display data on said measurement picture, and means for respectively storing said reduced image display data of each image in said memory unit with the respective measurement conditions of each image at the time said reduced image display data is created by said scale-down imaging process.

3. An ultrasonic inspection and imaging instrument as claimed in claim 1, wherein said processor unit has a microprocessor unit including means for accessing said memory unit.

4. An ultrasonic inspection and imaging instrument as claimed in claim 3, wherein said memory unit includes means for storing a processing program for displaying the plurality of images without being overlapped on the display screen according to the plurality of image data stored in said memory unit, a processing program for obtaining from said memory unit the measurement conditions stored corresponding to said image data corresponding to said selected image, and a processing program for displaying the measurement picture of an object under examination on the display screen of said display by subjecting the object under examination to said two-dimensional scanning, and wherein these three processing programs are selectively executed by said microprocessor unit.

5. An ultrasonic inspection and imaging instrument as claimed in claim 1, further comprising scanning means for two-dimensionally scanning the object under examination and for outputting image data from a plurality of scanned measuring points of the object, means for receiving the image data and for determining measured values from the respective scanned measuring points, and means for deriving the measurement picture from the measured values.

6. An ultrasonic inspection and imaging instrument as claimed in claim 5, wherein said measured values are the peak values of the respective scanned measuring points.

7. An ultrasonic inspection and imaging instrument for detecting an echo obtainable from an object under examination by two-dimensionally scanning the object under examination using an ultrasonic probe to obtain a measured value and for creating display data according to the measured value in order to display, on a screen, a measurement picture of the object under examination corresponding to said two-dimensional scanning, said instrument comprising:

a scanning mechanism for two-dimensionally scanning the object under examination;

an image processor unit having a display, a memory unit and a processor unit; said processor unit including means for controlling said scanning mechanism to two-dimensionally scan the object under examination, means for collection a plurality of measured values during the scanning, means for creating said display data corresponding to the two-dimensional scanning, and means for displaying said measurement picture on the screen of said display; said processor unit further having means for creating reduced image display data resulting from scaling down to 1/n (n=integer greater than 2) the display data of said measurement picture obtained in conformity with the predetermined measurement conditions so as to store said display data in said memory unit with respective measurement conditions at the time the display data is created by said reduced image processing; said image processor unit further including means for displaying a plurality of reduced images, without being overlapped, according to the plurality of reduced image display data stored in said memory unit, means for obtaining the measurement conditions stored corresponding to said reduced image of said reduced image display data, and means for displaying the measurement picture of an object under examination on the screen of said display by subjecting the object under examination to two-dimensional scanning by said scanning mechanism in accordance with a user-indicated one of the displayed reduced images.

8. An ultrasonic inspection and imaging instrument as claimed in claim 7, wherein said processor unit has a microprocessor unit including means for accessing said memory unit.

9. An ultrasonic inspection and imaging instrument as claimed in claim 8, wherein said memory unit includes means for storing a processing program for creating reduced image display data resulting from scaling down to 1/n (n=integer greater than 2) the display data on said measurement picture obtained in conformity with the predetermined measurement conditions so as to store said display data in said memory unit with respective measurement conditions at the time the display data as an object for said reduced image processing is obtained; a processing program for displaying a plurality of reduced images without being overlapped according to the plurality of reduced image display data stored in said memory unit; a processing program for obtaining the measurement conditions stored corresponding to said reduced image of said reduced image display data; and a processing program for displaying the measurement picture of the object under examination in accordance with the display data obtained from the two-dimensional scanning, and wherein these four processing programs are selectively executed by said microprocessor unit.

10. An ultrasonic inspection and imaging instrument as claimed in claim 9, wherein n represents an integer selected from among 5 to 15.

11. An ultrasonic inspection and imaging instrument as claimed in claim 10, further comprising an input unit for providing an input signal for indicating one of the displayed reduced images, wherein said input unit is a touch sensitive screen.

12. An ultrasonic inspection and imaging instrument as claimed in claim 9, further comprising an input unit for providing an input signal for indicating one of the displayed reduced images, wherein said input unit is either a mouse or a keyboard.

13. An ultrasonic inspection and imaging instrument as claimed in claim 9, further comprising touch-sensitive means associated with said display screen for selectively implementing at least one of the four processing programs for execution by said microprocessor unit.

14. An imaging system for two-dimensionally scanning an object under examination to obtain display data, and for displaying a measurement picture of the object under examination corresponding to said two-dimensional scanning, said system comprising:

a memory unit for storing data of a plurality of images and a plurality of measurement conditions corresponding to said plurality of images, including measurement conditions under which said measurement picture is obtained;

a processor unit for concurrently displaying a plurality of images without being overlapped on a display screen according to the plurality of image data stored in said memory unit, for obtaining from said memory unit a measurement condition stored corresponding to image data of an image selected from said plurality of stored images, and for displaying the measurement picture of the object under examination on the display screen by subjecting the object under examination to said two-dimensional scanning in accordance with the selected image; and means for two-dimensionally scanning the object under examination responsive to a signal from the processor unit that automatically presets the scanner with the measurement conditions in accordance with a user-indicated one of the displayed images.

* * * * *